(12) United States Patent
Zotti et al.

(10) Patent No.: US 7,094,261 B2
(45) Date of Patent: Aug. 22, 2006

(54) DOUBLE LAYER SURGICAL MESH

(75) Inventors: Gian Carlo Zotti, Naples (IT); Massimo Mancuso, Naples (IT)

(73) Assignee: Angiologica B.M. SRL, Siccomario (IT)

( * ) Notice: Subject to any disclaimer, the term of this patent is extended or adjusted under 35 U.S.C. 154(b) by 0 days.

(21) Appl. No.: 10/275,839

(22) PCT Filed: May 5, 2001

(86) PCT No.: PCT/IB01/01301

§ 371 (c)(1), (2), (4) Date: Mar. 10, 2003

(87) PCT Pub. No.: WO01/85058

PCT Pub. Date: Nov. 15, 2001

(65) Prior Publication Data
US 2003/0171823 A1 Sep. 11, 2003

(30) Foreign Application Priority Data
May 5, 2000 (IT) .......................... MI2000A0982

(51) Int. Cl.
*A61F 2/02* (2006.01)

(52) U.S. Cl. .............................. 623/23.72; 623/23.64; 606/151

(58) Field of Classification Search ............... 606/151; 623/23.64, 23.72, 23.74, 23.76
See application file for complete search history.

(56) References Cited

U.S. PATENT DOCUMENTS

| 3,286,713 | A | * | 11/1966 | Kurtz et al. | 604/180 |
| 4,854,316 | A | * | 8/1989 | Davis | 606/153 |
| 6,174,320 | B1 | * | 1/2001 | Kugel et al. | 606/151 |
| 6,258,124 | B1 | * | 7/2001 | Darois et al. | 623/14.13 |
| 2003/0212460 | A1 | * | 11/2003 | Darois et al. | 623/23.64 |

FOREIGN PATENT DOCUMENTS

| EP | 719527 A1 * | 7/1996 |
| EP | 827724 A2 * | 3/1998 |
| FR | 2837091 A1 * | 9/2003 |

OTHER PUBLICATIONS

Translation of French Patent Document No. 2,744,906.*

* cited by examiner

*Primary Examiner*—David H. Willse
*Assistant Examiner*—Javier G. Blanco
(74) *Attorney, Agent, or Firm*—Ladas & Parry

(57) ABSTRACT

A mesh (1) made of monofilament polypropylene (PPL) with surgical quality (CQ) and controlled flat memory (CM), having upper (1') and lower (1") layers joined by welding along almost the entire length of their edges (p). The layers have equal coaxial holes (2', 2") for passage of the spermatic cord of a patient, two radial slits (3', 3") departing from said holes and forming an angle between 9° and 120°, the zone (q) of the edges between the slits being free so as to create an upper (5') and a lower (5") fins that can be easily bent.

10 Claims, 3 Drawing Sheets

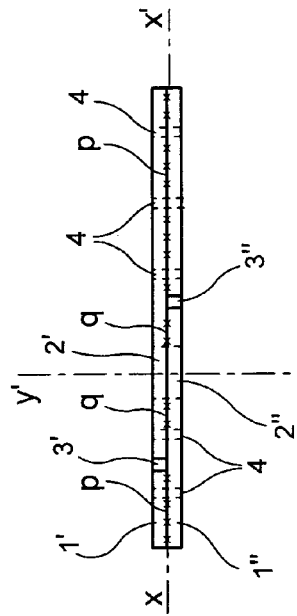
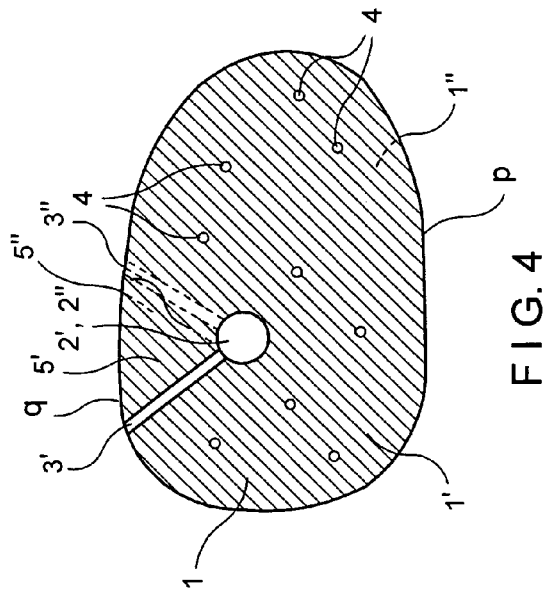
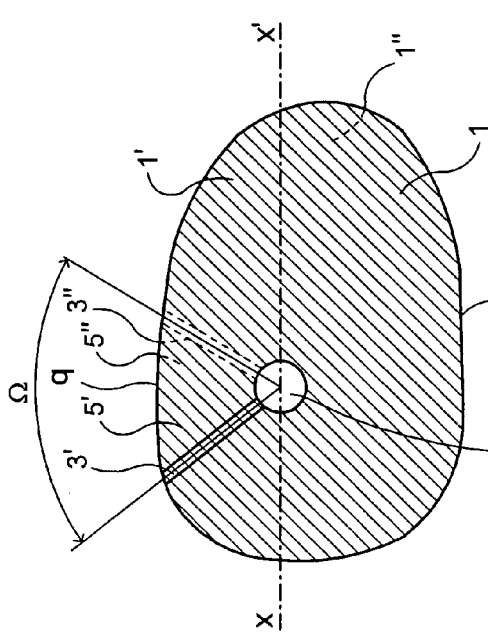
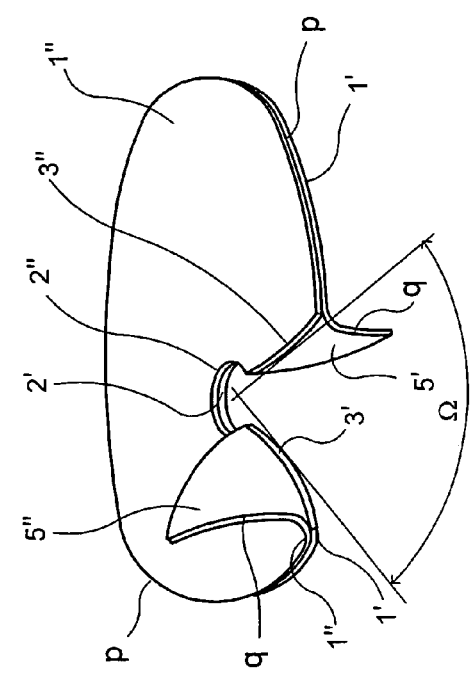
FIG. 1
FIG. 2
FIG. 3
FIG. 4

DOUBLE LAYER SURGICAL MESH

The present invention relates to a double layer anatomic surgical mesh.

More particularly the invention relates to a surgical mesh for its application inside the human body, with ideal biocompatibility and stiffness characteristics, and of a proper anatomic shape, mainly to solve the problems relating to hernia surgery in hernioplasty operations.

A fundamental problem of hernia surgery is their relapse; another fundamental problem is not to harm the spermatic cord and or to damage or contuse it after operation.

Therefore particular care should be taken besides the method used, in carrying out a prosthesis for hernioplasty as to shape, size and characteristics of the material.

The most spread technique in hernia surgery was the most frequently used Bassini-Shouldice method of direct tissular suture.

The introduction of wall reinforcing prostheses firstly of the Marlex-Prolene type and then made of PPL (polypropylene) and the consequent evolution of their anatomic shape, coupled with the contemporaneous introduction of new surgical techniques, allowed to develop a new approach to hernia pathology either in the form of "day surgery", namely without post-operative stay, or the increase of percentage of patients facing such an operation as soon as the affection is diagnosed trusting in quickness, simplicity and efficiency of the new techniques, or the surgeon extension of the operation also to patients that for a serious deterioration of the general conditions would not be able in the past to face such surgical treatment.

As above stated, the fundamental problem is to prevent relapses.

The reasons of the relapses are mainly the mesh misplacement due to migration, deformation or crumpling of the mesh; its suture and fixing to the wall that may cause an erroneous distribution of tensions; generation of dead space and serum accumulation; hematomas that may displace the prosthesis; preparing and positioning the spermatic cord; incorrect shape and size of the mesh; a slow or moderate fibroplastic infiltration; in order to avoid the above mentioned drawbacks prostheses of various materials and shapes of surgical quality (CQ) were introduced, that is biocompatible meshes keeping all their characteristics of stability of physico-chemical and dimensional parameters, (elasticity, resistance, flexibility, stiffness, wear, thickness, porosity, transparency) after sterilization in autoclave and with ethylene oxide and after implant, and with controlled memory (CM), that is adapted to keep a surface memory maintaining resistance to crumpling.

Monofilament polypropylene (PPL) resulted to be the material most adapted for the above mentioned requirements and therefore preferred by surgeons.

This material has high tensile resistance, is biologically stable, well tolerated and does not produce allergic response, is not carcinogenic, resistant to infections just because of the monofilamentary characteristics, produces a quicker fibroplastic proliferation leading to a more efficient collagene deposition.

These characteristics may be obtained only with proper mechanical and thermal treatments of the material for the polypropylene mesh, such as spinning, weaving, texture, filament diameter, thickness, roughness, pore size and the corresponding treatments, pretensioning and preheating in addition to those for increasing thermal stability and final treatments to obtain ideal stiffness and memory.

Indeed the disadvantages of this material are thermolability and memory at the autoclave sterilization temperatures at 126° C., at which the mesh undergoes a deformation taking into account that polypropylene has a melting point of about 165° C.

A mesh without memory control tends to crumple and to be incorrectly positioned, said misplacements occurring during or after implant causing dead space, serum generation, mesh migration and therefore risk of relapse.

It is therefore clear that the surgical characteristics to be met by the mesh, namely long term dimensional stability, elasticity, resistance and ability to comply with movements and contractions of the muscles, will depend mainly upon accuracy of working and treatment carried out on the mesh.

A too soft mesh for obtaining a starting good fit is likely to crumple subsequently even during operation, a too rigid mesh will find a difficult fit so as to induce subsequent troubles, tingles, twinges or reactions in the patient.

Another decisive feature of the mesh is its shape primarily dictated by the anatomic need of meeting the existing pathology, but also by practicality of manipulation and positioning during the implant operations according to the used operation technique.

From shaping carried out mostly manually at the operating theater one passed to use industrially preshaped prostheses, with advantages of greater warrant of sterility in view of less manipulation needed; atraumatic character and resistance in view of the finishing treatment of the edges, which are smooth, not sharp and without ravel; and optimal shape standardization, as it is possible to use a set of standard sizes, meeting the various kinds of the patient's pelvis and tested immediately without waiting times during operation.

In order to avoid relapse caused by tensions generated by the sutures of the mesh as prosthesis of the implant one passed to new meshes and operative techniques, such as "tension free sutureless mesh" and "sutureless tension free repair" or "sutureless tension free hernioplasty mesh", see "Prostheses in abdominal wall hernias by Robert Bendavid (1994) and European patent application of Trabucco, No. 97 115149 (publ. N. 0827724) corresponding to Italian utility model No. 232435.

This technique consists in implanting in a closed anatomic space, namely the inguinal canal a preshaped mesh with hole and slit at the spermatic cord, of standard size adapted to fit into said space in an optimal way. In this way it is not necessary to suture the mesh, which is prevented from moving inside a closed anatomic space by fascial and aponeurotic tissues still remaining tension free and without forming dead space.

A mesh sutured to tissues may produce an erroneous distribution of tensions and generate dead space; a sutureless mesh is always tension free and does not generate dead space.

The feature of this mesh is to have a well determined single standard size (10×4.5 cm, hole diameter 1–1.2 cm) because the author believes according to observation of an extended survey and anatomic measurements, that the dimensions of the inguinal wall have no considerable variations according to the kind of patient.

Another manufacturers put on the market the same kind of the preshaped mesh, with or without hole and slit, hernia prostheses with opening for the spermatic cord, with similar or equal shape and almost identical dimensions or anyway not far from the values of the inguinal box, see for instance the meshes of Bard or "Premilene" of Brown or "Trelex" made by Medox and so forth).

With this technique aponeurosis of the external oblique muscle is cut longitudinally, the cremasteric muscle is parted and opened longitudinally; then one proceeds to isolate the mesentery of the spermatic cord and its raising. The hernial sac is isolated, introflexed, reduced or surgically treated.

After reconstruction of the floor of the inguinal canal a rigid mesh with preshaped form and size provided with an opening for the spermatic cord is prepared and positioned above the fascia trasversalis in a closed anatomic space. It is not necessary to suture the mesh except closing its opening. The aponeurosis of the external oblique muscle is finally closed under the spermatic cord without tension because the inferior crus was widened by dissection.

As to the position of the spermatic cord, it may be under or above aponeurotic: when the spermatic cord is in a under aponeurotic position, the mesh is in contact only with fascia trasversalis at the medial portion of the inguinal canal; when the spermatic cord is in an above aponeurotic position, the mesh is-in contact with two layers, the fascia trasversalis under and aponeurosis of the external oblique muscle above, so as to form a triple stronger layer just where relapses are more frequent.

The opening or slit for the spermatic cord may be left free or sutured. However in the first case the fins tend to spread so as to compromise their seal and allowing a displacement or causing damage to the spermatic cord; in the second case dihedral bending along the slit is promoted, inducing formation of dead space and generation of a relapse start, as well as possible damage of the spermatic cord.

This method is successfully applied to hernioplasty for external oblique, inguinal, crural, inguino-crural herniae with inguinal approach and front repair; such a method however does not solve the problem of deformation and migration of the mesh either by straddling of the fins when left free or by bending of the fins when joined with a suture stitch at the slit, hindering the mesh to stay flat.

Moreover the problems connected with the consequent risk of damage of the spermatic cord are not solved.

This kind of mesh therefore does not remove completely the risk of reappearance of relapsing herniae.

In order to remove the drawbacks of the prior art the present invention relates to a mesh for repairing surgically weak or collapsed tissues, more particularly in hernioplasty, having ideal shape, size, characteristics, stiffness and controlled memory.

As above mentioned lability of the fins created by the slit of the opening for the spermatic cord either by their straddling or their bending is the main reason of relapse.

Thanks to applicant the present invention consists in creating a double layer mesh, comprising two overlapping layers with equal coaxial holes and radial diverging slits, said layers being joined along the entire contour edge with the exception of the zone defined by the two slits, in order to create two fins that are initially overlapping but during operation are bent passing the upper fin below and the lower fin above like the tabs of a box or carton at its closure.

In this way like in the above example of the carton the closure is blocked without requiring adhesive tape or metal staples, in case of the prosthesis of the invention the mutual tucking of the fins blocks the mesh at the spermatic cord without damaging it and without needing mutual suture of the fins at said slits.

The double layer confers to the mesh a greater stiffness without decreasing its ability to fit to the tissues, obtaining a better memory control to avoid its crumpling or misplacement.

To avoid a possible slower fibroplastic infiltration caused by the gap of the double layer, this is balanced by an increased uniform macroporosity of the mesh, also as a function of its thickness, when treating the monofilament mesh, as well as by making additionally on the mesh supplementary through holes of suitable shape, size, number and position.

This mesh allows also the implant by operation with properitoneal (rear) approach even with the laparoscopic technique.

More particularly the present invention relates to a prosthesis made of a double layers preshaped surgical mesh, characterized by comprising two mesh layers, each comprising a hole of the same diameter connected to a corresponding opening, said layers being sandwich overlapped so that said holes are coaxially coincident, while said openings are arranged according to divergent lines forming a predetermined angle.

Some preferred non limiting embodiments of the invention will now be described hereinafter.

The prosthesis of the invention is characterized in that the overlapping upper and lower layers are connected along their outer edge with the exception of the zone between the two openings or slits, so as to form corresponding upper and lower free fins, the lower fin being bent upwards and the upper fin downwards so that the lower fin is tucked above the upper fin obtaining the mesh selfblocking.

The mesh is also characterized in that the slits connecting the holes of each layer to the corresponding outer edge, are cut on each layer according to diverging radial directions so as to form an angle between 90° and 120°.

In the mesh according to the invention the two layers are joined along their contour with the exception of the portion corresponding to the fins, by laser welding so as to obtain fully smooth polished, non sharp edges without ravel.

In another embodiment the two layers are welded not only at the corresponding edge length, but also on their entire contact surface with the exception of the zones of the fins.

This modified embodiment allows to carry out oversized prostheses, that can then be cut by the surgeon when implanting the mesh during the operation so as to obtain from the standard shape a custom made mesh for the patient, perfectly adapted and responding to his needs.

The mesh according to the invention is made of monofilament polypropylene (PPL) of surgical quality (CQ) and controlled memory (CM) with ideal resistance, elasticity, roughness and stiffness.

The surgical quality (CQ) means that the mesh meets the criteria of biocompatibility and thermal stability and have high macroporosity for promoting a quick fibroplastic infiltration.

The macroporosity of said mesh is the result of the working treatments and of the holes added passing through the double layer, said holes having shape, size, diameter, number, uniform arrangement that are optimal relative to the thickness of said double layer, to balance and increase the fibroplastic infiltration slowed by the gap of the double layer and at the same time keeping the ideal stiffness, respectively.

The controlled memory means the ability of the mesh to keep its shape without crumpling tendency while keeping the fitting ability. The mesh is preferably available for use with controlled flat memory.

The present invention relates also to the use of said mesh in the surgery of herniae, more particularly in hernioplasty with properitoneal (rear) approach, even of the laparoscopic and open kind, with mesh implant.

A description of a preferred non limiting example of the mesh of the present invention is given hereinafter with reference to the figures of the accompanying drawings, however without diminishing the general scope of the invention.

FIG. 1 is a plan view of the mesh of the invention;

FIG. 2 is a sectional side view of the mesh;

FIG. 3 is a perspective view of the hernial prosthesis with overturned mesh to better show the movement of the fins, the lower fin being raised and the upper fin being lowered respectively, their tucking action being obtained by bending the fins in the direction opposite to that shown in drawing;

FIG. 4 is a plan view of the prosthesis of the invention provided with through holes for increasing the fibroplastic infiltration;

The mesh 1 made of monofilament polypropylene (PPL), of surgical quality (CQ) and controlled flat memory (CM) consists of upper 1' and lower 1" layers joined by welding along almost the entire length of the edges p, with the exception of the zone q corresponding to the fins 5', 5", that are smooth, polished and without ravel as shown in FIGS. 1 and 2. Said layers comprise identical coaxial holes 2', 2" from which two radial openings or slits 3', 3" lead off forming an angle $\Omega$, comprised between 90° and 180°; the zone of the edges q between said slits is not joined but is free generating an upper 5' and lower 5" fin that can be easily bent as shown in FIGS. 1, 2 and 3.

By bending said fins, lowering the upper fin and raising the lower fin respectively, they are firstly opened so as to make easier the subsequent bending and closure tucking the lower fin above the upper fin by overlapping and this movement is shown for sake of clarity with the overturned mesh in FIG. 3.

In this way during the operation a perfect dimensional stability of the mesh prosthesis is obtained, without undesired deformations, but still capable of the required elasticity, bending and fitting, and with the ideal stiffness and memory control as well.

Figure 5:
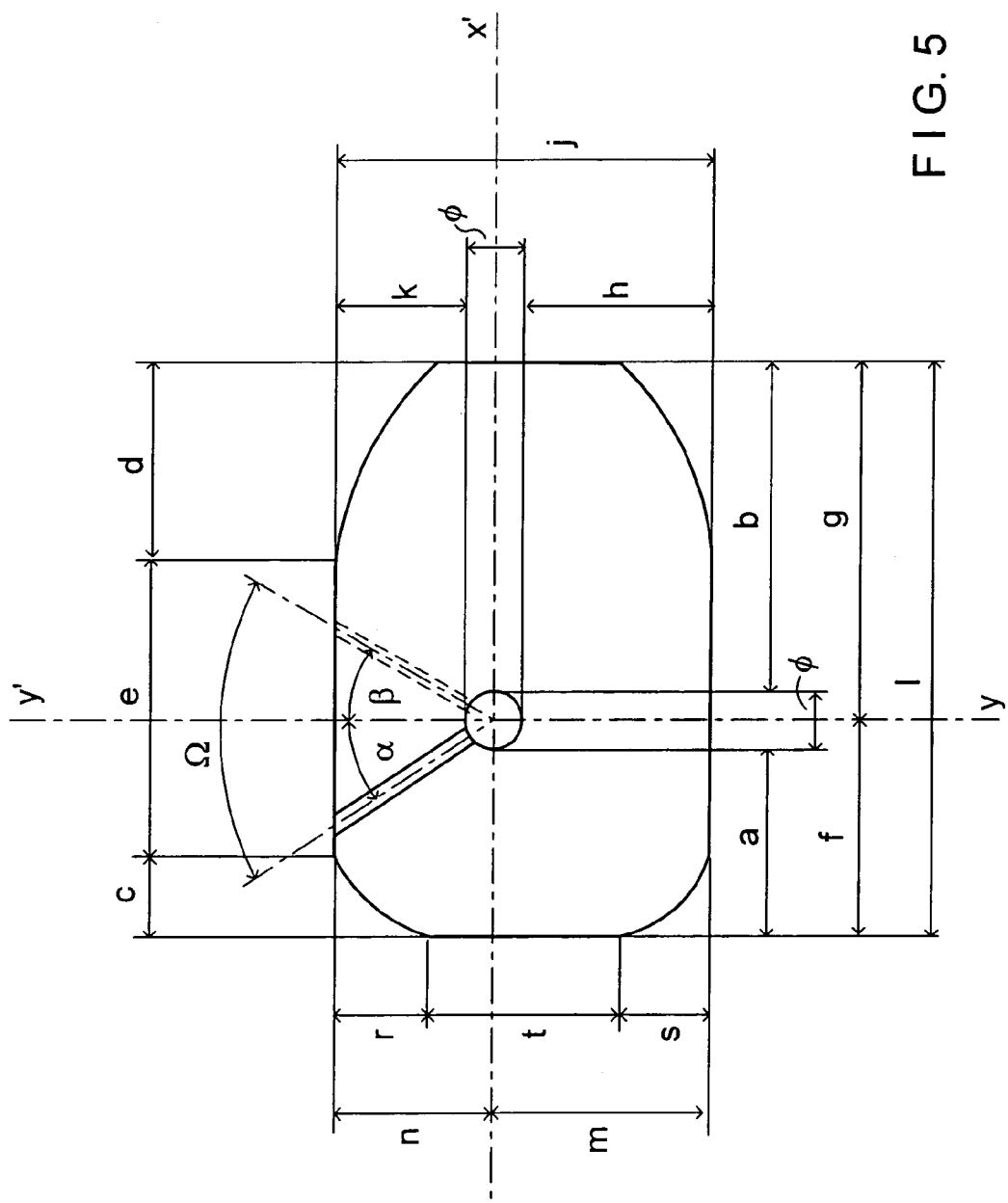
FIG. 5 is a plan view of the prosthesis with the parameters defining its characteristic size.
Figure 6:
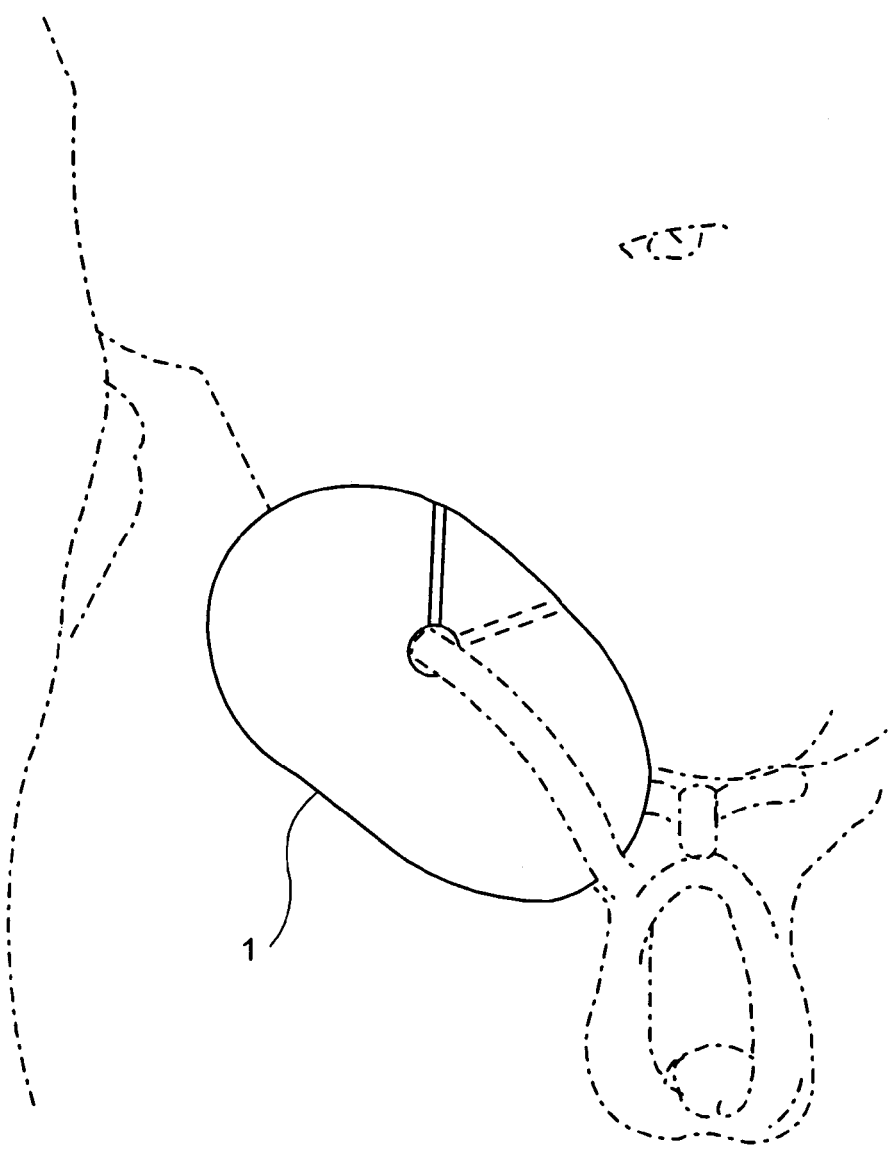
FIG. 6 shows the position of the prosthesis around the spermatic cord in a hernioplastic implant.

A preferred embodiment has an anatomic shape with the following characteristic dimensions or sizes with reference to the axes xx', yy': length l=12 cm; height j=8 cm; horizontal distance from hole a=7 cm; b=4 cm; horizontal distance from hole center f=7.5 cm; g 4.5 cm; vertical distance from hole h=4 cm; k=3 cm; hole diameter $\varnothing$=1 cm; angle between the fins $\Omega$=90°; angle of the fins with the vertical axis yy' $\alpha=\beta=45°$; starting distance of rounding from the vertical side edges c=d=4 cm; horizontal distance between rounding start e=4 cm; starting distance of rounding from horizontal edges r=s=2 cm; vertical distance between start of vertical roundings t=4 cm; see FIG. 5.

A second preferred embodiment has an anatomic shape with the following characteristic size or dimensions: l=11 cm; j=7 cm; $\varnothing$=1 cm, with the same values of the above mentioned angles and proportional reduction of all the other dimensions of FIG. 5.

Since the suture of the openings is not required in this kind of mesh, which is the primary reason of the relapses for lack of ability of the mesh to stay flat in the prior art known meshes, bending and formation of dead space and serum accumulation are avoided. Moreover the self blocked mesh allows to carry out a perfect sutureless tension free operation, the tension being another primary relapsing factor.

The double layer allows to obtain more stiffness, because a soft mesh is easier to crumple and migrate, but induces a slower fibroplastic infiltration created by the gap or dead space of the double layer and therefore less resistance to infections; this drawback is balanced by the macroporosity of the mesh and the supplemental holes added with uniform shape, size, diameter, number and arrangement relative to the thickness, bringing the capability of infiltration of the mesh of the invention to the same levels of the prior art single layer meshes or even increasing such a level.

A variation of this mesh indeed has holes 4', 4" passing through the double layer like a colander, in order to increase the fibroplastic infiltration and collagene deposition for avoiding infections and post operative complications as well as a quicker recovery of the patient, see FIGS. 2 and 4.

Generally the supplemental holes have a diameter of 1 mm, and their number is preferably comprised between 6 and 10, see FIGS. 2 and 4.

Hernioplasty with properitoneal approach and mesh implant will now be described.

Patients and Methods

From table 1 hereinbelow the rate of complications and relapses in the various types of hernia repair is reported.

TABLE 1

| Authors | Techniques | Complications | Relapses |
|---|---|---|---|
| | Hernia repair with suture, without prosthesis | | |
| Hay, 1995 | Bassini | 27% | 8.6% |
| Emmanoulidis, 1993 | Shouldice | 19% | 3% |
| Hay, 1995 | | | |
| Kingsnorth, 1992 | | | |
| | Prosthetic front approach | | |
| Wantz, 1996 | Liechtenstein | 12% | 0.5% |
| Campanelli, 1993 | Trabucco | 12% | 1.5% |
| | Prosthetic preperitoneal approach | | |
| Stoppa, 1989 | Stoppa | 3,5% | 1.1% |
| Topla, 1997 | Rignault | 2% | 2% |
| Rignault, 1986 | | | |

The personal experience consists of a survey in which 2670 patients with pathology of inguinal hernia were recruited and operated. The operations mostly effected in the operating theaters of the general surgery department of the polyclinic hospital of the Naples University, were made exclusively by the authors during the years with several techniques as reported in table 2.

TABLE 2

| Techniques used in effecting herniarraphy | | |
|---|---|---|
| Period | Technique | Patients |
| 1976–1981 | Bassini | 315 |
| 1982–1988 | Shouldice | 1007 |
| 1989–1993 | Trabucco | 639 |
| 1994–1999 | Properitoneal mesh | 709 |

In this survey only adult patients (388) operated in the three years period 1994–1996 will be taken into account, because they were sufficiently homogeneous and underwent a follow up program completed last year with 86% of patients (344) checked at the four scheduled appointments and 100% checked in at least three appointments out of four.

From January 1994 to December 1996 388 adult patients, of which 372 male (96%) and 16 female (4%) with an average age of 62.7 years (range 29–88), were operated for hernioplasty by applying the mesh through the properitoneal route.

Among the patients, 216 (56%) had an indirect hernia, 94 (24%) a direct hernia and 78 (20%) a double (direct and indirect) hernia. 22%, namely 85 patients, had multiple herniae (15% bilateral hernia and 7% equal to 27 patients had a homolateral inguinal and crural multiple hernia). No patient had hernia of crural type only. 31 cases (8%) were a relapse of inguinal or femoral hernia.

The used prosthesis is an industrial preshaped polypropylene mesh of various size according to the type of the patient's pelvis. The mesh was produced according to our specifications (shape, thickness and texture), identified on the basis of the surgical experience completed in these operations. The choice of preferring industrial preshaped polypropylene mesh was dictated by the advantages of sterility (less manipulation), atraumatic character, resistance, welded mesh edges) and standardization of the shape offered by this kind of product in comparison with the mesh manually preshaped in the operating theater by the surgeon with relevant loss of time.

The operation was carried out by making a transversal cut about 1–2 inches below the front upper iliac spine of an average length of 5–6 cm. Having taken apart the lateral muscles of the abdomen, one proceeds to decollement of the peritoneal sac, locating the iliac vessels, the crural ring and above the inguinal ring. The hernial sac is then reduced and of course also those associated with various direct and/or crural herniae and is isolated by displacing maneuvers from funiculus and from properitoneal fat of the rear wall of the inguinal canal up to the genital tubercle taking special care of the frequent little inflammatory lipomas existing at the crural ring, generally adhering to the iliac vein that must be cautiously removed, because they play a non negligible role in the possible generation of a relapse.

At this point the suitable size of prosthesis is chosen, a vertical cut of 2–3 cm is made on the upper edge through which the funiculus is being passed and then the prosthesis is positioned in such a way to cover the entire inner face of the rear inguinal wall with a little length of lower extension on the iliac vessels at the juxtacrural level.

The ideal shape and size of the prosthesis mesh is very debated, and our experience supports our choice of shape, size, thickness and quality of the polypropylene mesh used by us. This use showed that the type of mesh chosen by us optimizes the technique used in terms of surgical procedure and results.

In our opinion as cornerstones the general principles of surgery are maintained: a good haemostasis, an accurate isolation of the anatomic structures, a correct application in positioning the mesh taking care that the mesh is unfolded in a perfectly flat way without forming folds or pleats.

It was our care to pay special attention to haemostasis because hematomas are one of the reasons of relapse since they can displace the prosthesis. Wantz recommends, when haemostasis would result incomplete or when there is a sac retention of big size where there is blood accumulation, to use drainage. We never used any drainage.

In 39 patients (10%) general anaesthesia was used, generally upon their explicit request. In 349 patients (90%) a local regional anaesthesia was effected (330 with spinal infiltration 19 with local infiltration). In any case the type of anesthesia has no relation with relapses.

Duration of surgery was as an average 40 minutes (range 30–70 minutes). The patients received on request post operative analgesic therapy based on "Ketorolac" 30 mg i.m. at 4–6 hours from operation and in 384 cases (98%) were discharged the first day.

The inventin claimed is:

1. In a method for performing hernia surgery on a patient wherein a mesh is positioned in the inguinal canal of the patient to help avoid a hernia relapse, the improvement comprising (a) providing a prosthesis comprising a pre-shaped surgical mesh having upper and lower mesh layers, each of said upper and lower mesh layers defining a hole, an outer edge and a slit from the hole to the outer edge, said upper and lower mesh layers overlapping one another with the hole of the upper mesh layer coaxially coincident with the hole of the lower mesh layer and with the slit of the upper mesh layer diverging from the slit of the lower mesh layer at an angle so as to define a zone between the respective slits of the upper and lower mesh layers around which the outer edge of the upper mesh layer is not joined to the outer edge of the lower mesh layer, the upper and lower mesh layers being otherwise joined along their respective outer edges, and so as to form an upper fin in the upper mesh layer and a lower fin in the lower mesh layer, wherein the upper and lower fins are bendable in respective downward and upward directions such that the lower fin can be tucked and overlapped above the upper fin to provide for self-blocking of the prosthesis; and (b) implanting the prosthesis into the patient with the coaxially coincident holes of the upper and lower mesh layers around the spermatic cord of the patient and with the lower fin tucked and overlapped above the upper fin.

2. The method according to claim 1, wherein, in the prosthesis, the angle is between 90 and 120 degrees.

3. The method according to claim 1, wherein, in the prosthesis, the angle is between 90 and 180 degrees.

4. The method according to claim 1, wherein, in the prosthesis, the respective outer edges of the upper and lower mesh layers which are otherwise joined are joined by laser welding.

5. The method according to claim 4, wherein, in the prosthesis, the upper and lower layers are welded to each other along their entire surfaces with the exception of surfaces of the upper and lower fins.

6. The method according to claim 1, wherein, each of the upper and lower mesh layers comprises monofilament polypropylene of surgical quality and controlled memory.

7. The method according to claim 6, wherein each of the upper and lower mesh layers has controlled flat memory.

8. The method according to claim 1, wherein said prosthesis comprises a plurality of supplemental holes passing through said upper and lower mesh layers to allow for increased fibroplastic infiltration.

9. The method according to claim 8, wherein the prosthesis comprises between 6 and 10 of the supplemental holes.

10. The method according to claim 9, wherein each of the supplemental holes has a diameter of 1 mm.

* * * * *

UNITED STATES PATENT AND TRADEMARK OFFICE
CERTIFICATE OF CORRECTION

PATENT NO. : 7,094,261 B2 Page 1 of 1
APPLICATION NO. : 10/275839
DATED : August 22, 2006
INVENTOR(S) : Gian Carlo Zotti et al.

It is certified that error appears in the above-identified patent and that said Letters Patent is hereby corrected as shown below:

On title page, item 57, "9°" should read -- 90° -- and, last line, delete "an" and "a".

Signed and Sealed this

Third Day of April, 2007

JON W. DUDAS
*Director of the United States Patent and Trademark Office*